US012672835B2

(12) United States Patent
Saito

(10) Patent No.: US 12,672,835 B2
(45) Date of Patent: Jul. 7, 2026

(54) X-RAY CT APPARATUS, DATA PROCESSING METHOD, AND STORAGE MEDIUM

(71) Applicant: CANON KABUSHIKI KAISHA, Tokyo (JP)

(72) Inventor: Yasuo Saito, Nasushiobara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 102 days.

(21) Appl. No.: 18/528,883

(22) Filed: Dec. 5, 2023

(65) Prior Publication Data

US 2024/0188912 A1     Jun. 13, 2024

(30) Foreign Application Priority Data

Dec. 8, 2022     (JP) ................................. 2022-196200

(51) Int. Cl.
| | |
|---|---|
| *A61B 6/42* | (2024.01) |
| *A61B 6/00* | (2024.01) |
| *A61B 6/03* | (2006.01) |
| *G01T 1/17* | (2006.01) |

(52) U.S. Cl.
CPC ............ *A61B 6/4241* (2013.01); *A61B 6/035* (2013.01); *A61B 6/4435* (2013.01); *A61B 6/54* (2013.01); *G01T 1/17* (2013.01)

(58) Field of Classification Search
CPC ..... A61B 6/035; A61B 6/4241; A61B 6/4435; A61B 6/54; G01T 1/17
See application file for complete search history.

(56) References Cited

U.S. PATENT DOCUMENTS

| | | | | |
|---|---|---|---|---|
| 7,403,589 | B1* | 7/2008 | Short .................... | G01T 1/1642 |
| | | | | 250/370.11 |
| 9,851,460 | B1* | 12/2017 | Rodrigues ............... | G01T 1/247 |
| 2007/0076842 | A1* | 4/2007 | Tkaczyk .............. | A61B 6/4085 |
| | | | | 378/108 |
| 2007/0205367 | A1* | 9/2007 | Deman .................. | A61B 6/482 |
| | | | | 250/366 |
| 2007/0206721 | A1* | 9/2007 | Tkaczyk ................. | G01T 1/249 |
| | | | | 378/19 |

(Continued)

FOREIGN PATENT DOCUMENTS

| | | | |
|---|---|---|---|
| JP | 2018-175866 A | | 11/2018 |
| JP | 2022-26909 A | | 2/2022 |
| JP | 2022026909 A | * | 2/2022 |

OTHER PUBLICATIONS

Extended European Search Report issued Apr. 4, 2024 in European Patent Application No. 23214757.9, 8 pages.

*Primary Examiner* — Blake C Riddick
(74) *Attorney, Agent, or Firm* — Oblon, McClelland, Maier & Neustadt, L.L.P.

(57) ABSTRACT
An X-ray CT apparatus of an embodiment includes a gantry and a control device held by the gantry. The control device includes processing circuitry. The processing circuitry is configured to collect data corresponding to energy of a material, adjust conditions for the data at the time of collecting the data, bundle the data distinguished in some of a plurality of energy bins, aggregate the collected data and the bundled data, and switch between the aggregation of the collected data and the aggregation of the bundled data.

14 Claims, 8 Drawing Sheets

(56)  References Cited

U.S. PATENT DOCUMENTS

| | | | | |
|---|---|---|---|---|
| 2008/0099689 A1* | 5/2008 | Nygard | G01T 1/17 | 250/370.09 |
| 2008/0101535 A1* | 5/2008 | Wu | G01T 1/2985 | 378/19 |
| 2008/0175347 A1* | 7/2008 | Tkaczyk | G01T 1/24 | 378/7 |
| 2008/0230709 A1* | 9/2008 | Tkaczyk | G01T 1/249 | 250/370.09 |
| 2008/0240339 A1* | 10/2008 | Du | G01T 1/20184 | 250/363.02 |
| 2008/0240341 A1* | 10/2008 | Possin | H04N 25/773 | 250/370.11 |
| 2009/0039273 A1* | 2/2009 | Tkaczyk | G01T 1/247 | 250/370.06 |
| 2009/0052612 A1* | 2/2009 | Wu | G06T 11/008 | 378/5 |
| 2010/0329425 A1* | 12/2010 | Guo | G01T 1/247 | 378/91 |
| 2013/0148873 A1* | 6/2013 | Arenson | G06T 11/005 | 382/132 |
| 2013/0343517 A1* | 12/2013 | Gagnon | A61B 6/032 | 378/19 |
| 2014/0023181 A1* | 1/2014 | Noshi | A61B 6/482 | 378/91 |
| 2014/0328465 A1* | 11/2014 | Herrmann | G01T 1/2985 | 250/361 R |
| 2015/0085970 A1* | 3/2015 | Bouhnik | A61B 6/482 | 378/19 |
| 2015/0160355 A1* | 6/2015 | Wang | G01N 23/046 | 378/207 |
| 2015/0182176 A1* | 7/2015 | Jin | G01T 1/171 | 378/5 |
| 2015/0198725 A1* | 7/2015 | Tamura | G01T 1/17 | 378/5 |
| 2015/0250444 A1* | 9/2015 | Tamura | A61B 6/482 | 378/19 |
| 2015/0257722 A1* | 9/2015 | Wang | G01T 1/2985 | 250/336.1 |
| 2015/0297162 A1* | 10/2015 | Teshigawara | G02B 27/0944 | 378/5 |
| 2015/0327827 A1* | 11/2015 | Teshigawara | G01T 1/20184 | 250/362 |
| 2015/0374317 A1* | 12/2015 | Moriyasu | G01T 1/20183 | 378/5 |
| 2016/0022243 A1* | 1/2016 | Nakai | A61B 6/4085 | 378/5 |
| 2016/0029982 A1* | 2/2016 | Tamura | G01T 1/2018 | 378/19 |
| 2016/0054453 A1* | 2/2016 | Moriyasu | A61B 6/4035 | 378/19 |
| 2016/0058404 A1* | 3/2016 | Nitta | A61B 6/4241 | 382/131 |
| 2016/0070005 A1* | 3/2016 | Sagoh | G01T 1/20184 | 250/361 R |
| 2016/0081637 A1* | 3/2016 | Noshi | G01T 1/247 | 378/5 |
| 2016/0095561 A1* | 4/2016 | Tamura | A61B 6/032 | 378/62 |
| 2016/0131773 A1* | 5/2016 | Cao | A61B 6/4266 | 378/5 |
| 2016/0135778 A1* | 5/2016 | Roberts | A61B 6/4233 | 378/15 |
| 2016/0199016 A1* | 7/2016 | Wang | G01T 1/2985 | 378/19 |
| 2016/0203620 A1* | 7/2016 | Zou | G06T 11/003 | 378/19 |
| 2016/0206255 A1* | 7/2016 | Gagnon | G01T 1/00 | |
| 2016/0213340 A1* | 7/2016 | Zhang | G01T 1/2985 | |
| 2016/0242725 A1* | 8/2016 | Wang | A61B 6/4233 | |
| 2016/0300369 A1* | 10/2016 | Silver | G06T 5/20 | |
| 2016/0324493 A1* | 11/2016 | Rodrigues | G01T 1/2985 | |
| 2017/0086761 A1* | 3/2017 | Fu | A61B 6/4435 | |
| 2017/0086775 A1* | 3/2017 | Madhav | A61B 6/542 | |
| 2017/0090039 A1* | 3/2017 | Hoffman | A61B 6/42 | |
| 2017/0119340 A1* | 5/2017 | Nakai | A61B 6/50 | |
| 2017/0150932 A1* | 6/2017 | Kato | A61B 6/54 | |
| 2017/0212250 A1* | 7/2017 | Jin | G01T 1/20184 | |
| 2017/0238896 A1* | 8/2017 | Iwai | A61B 6/4035 | |
| 2017/0261620 A1* | 9/2017 | Kato | G01T 1/171 | |
| 2017/0290555 A1* | 10/2017 | Iniewski | H03K 23/40 | |
| 2017/0322319 A1* | 11/2017 | Iniewski | G01T 1/24 | |
| 2018/0192977 A1* | 7/2018 | Jin | G01V 5/22 | |
| 2018/0211417 A1* | 7/2018 | Miyazaki | G01N 23/046 | |
| 2018/0220979 A1* | 8/2018 | Kojima | A61B 6/542 | |
| 2018/0224564 A1* | 8/2018 | Fu | G01T 1/247 | |
| 2018/0242927 A1* | 8/2018 | Nakai | G01T 1/2985 | |
| 2018/0252821 A1* | 9/2018 | Svensson | G01T 1/18 | |
| 2018/0259657 A1* | 9/2018 | Fu | G01T 1/247 | |
| 2018/0300909 A1 | 10/2018 | Tamura et al. | | |
| 2019/0000409 A1* | 1/2019 | Tamura | A61B 6/545 | |
| 2019/0021685 A1* | 1/2019 | Kojima | A61B 6/4241 | |
| 2019/0021687 A1* | 1/2019 | Kato | A61B 6/4488 | |
| 2019/0150864 A1 | 5/2019 | Flohr et al. | | |
| 2019/0204456 A1* | 7/2019 | Persson | G01T 1/172 | |
| 2020/0069266 A1* | 3/2020 | Cai | A61B 6/4241 | |
| 2020/0158896 A1* | 5/2020 | Danielsson | G01T 1/243 | |
| 2020/0205751 A1* | 7/2020 | Taguchi | A61B 6/4452 | |
| 2020/0222024 A1* | 7/2020 | Edic | G01N 23/046 | |
| 2020/0323502 A1* | 10/2020 | Kojima | A61B 6/025 | |
| 2020/0330065 A1* | 10/2020 | Zhan | A61B 6/4035 | |
| 2020/0367836 A1* | 11/2020 | Kawata | A61B 6/587 | |
| 2021/0052236 A1* | 2/2021 | Nakai | G06N 5/04 | |
| 2021/0067710 A1* | 3/2021 | Steadman Booker | G01T 1/17 | |
| 2021/0085277 A1* | 3/2021 | Mirzaei | A61B 6/482 | |
| 2021/0121142 A1* | 4/2021 | Kawata | G01T 7/005 | |
| 2021/0219930 A1* | 7/2021 | Tsuchiya | A61B 6/4241 | |
| 2021/0239856 A1* | 8/2021 | Sjölin | G01T 1/247 | |
| 2021/0251588 A1* | 8/2021 | Kanai | A61B 6/58 | |
| 2021/0356609 A1* | 11/2021 | Kanai | G01T 1/247 | |
| 2022/0202383 A1* | 6/2022 | Okajima | A61B 6/4241 | |
| 2023/0404493 A1* | 12/2023 | Tsuyuki | A61B 6/5205 | |

* cited by examiner

Figure 4:
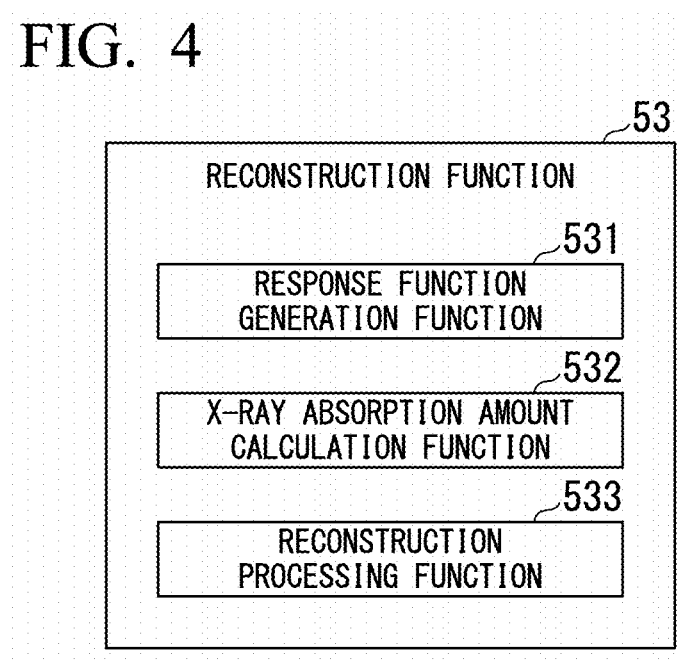

RECONSTRUCTION FUNCTION

531

RESPONSE FUNCTION
GENERATION FUNCTION

532

X-RAY ABSORPTION AMOUNT
CALCULATION FUNCTION

533

RECONSTRUCTION
PROCESSING FUNCTION

X-RAY CT APPARATUS, DATA PROCESSING METHOD, AND STORAGE MEDIUM

CROSS-REFERENCE TO RELATED APPLICATION

The present application claims priority based on Japanese Patent Application No. 2022-196200 filed Dec. 8, 2022, the content of which is incorporated herein by reference.

FIELD

Embodiments disclosed in this specification and drawings relate to an X-ray CT apparatus, a data processing method, and a storage medium.

BACKGROUND

As a detector in an X-ray computed tomography (CT) apparatus, for example, there are detectors that collect data by integrating the energy of X-rays and detectors that collect data by counting the number of X-ray photons for each of energies. Detectors that count the number of X-ray photons for each energy may process data for a plurality of energies in bundles.

Detectors that count the number of X-ray photons process enormous amounts of data, making it difficult to transmit the data in real time. The amount of transmission can be reduced by bundling all X-ray photons counted for each energy into one, for example. However, in this case, it is not possible to fully utilize the advantage of counting the number of X-ray photons for each energy, and it is difficult to make use of comparison with data obtained by integrating the energy of X-rays.

BRIEF DESCRIPTION OF THE DRAWINGS

FIG. 4 is a diagram showing an example of functional blocks of a reconstruction function 53 according to the first embodiment.

DETAILED DESCRIPTION

Hereinafter, an X-ray CT apparatus, a data processing method, and a storage medium according to embodiments will be described with reference to the drawings. The X-ray CT apparatus of the embodiments is a photon counting CT apparatus. The photon counting CT apparatus distinguishes materials through which X-rays have passed using a direct type detector.

An X-ray CT apparatus of an embodiment includes a gantry and a control device held by the gantry. The control device includes processing circuitry. The processing circuitry is configured to collect data corresponding to energy of a material, adjust conditions for the data at the time of collecting the data, bundle the data distinguished in some of a plurality of energy bins, aggregate the collected data and the bundled data, and switch between the aggregation of the collected data and the aggregation of the bundled data.

First Embodiment

Figure 1:
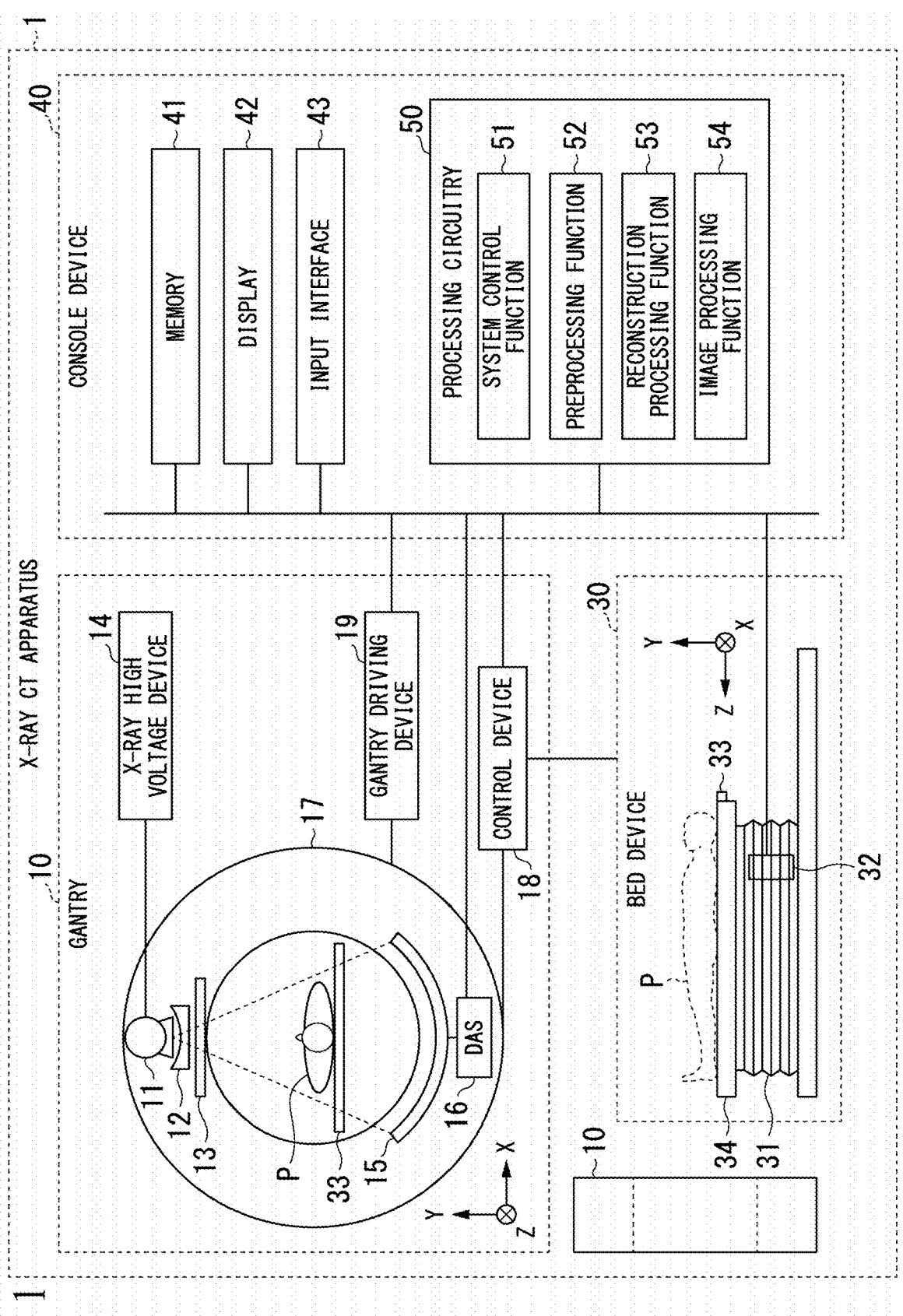
FIG. 1 is a diagram showing an example of an X-ray CT apparatus 1 according to a first embodiment.

FIG. 1 is a diagram showing an example of an X-ray CT apparatus 1 according to a first embodiment. The X-ray CT apparatus 1 includes, for example, a gantry 10, a bed device 30, and a console device 40. Although FIG. 1 shows both a view of the gantry 10 viewed in the Z-axis direction and a view of the gantry 10 viewed in the X-axis direction for convenience of description, in reality, there is only one gantry 10. In the embodiment, a rotation axis of a rotating frame 17 in a non-tilted state or the longitudinal direction of a top plate 33 of the bed device 30 is defined as the Z-axis direction, and the axis perpendicular to the Z-axis direction and horizontal to the floor surface is defined as the X-axis direction, and the direction perpendicular to the Z-axis direction and orthogonal to the floor surface is defined as the Y-axis direction.

The gantry 10 includes, for example, an X-ray tube 11, a wedge 12, a collimator 13, an X-ray high voltage device 14, an X-ray detector 15, and a data acquisition system (hereinafter, DAS) 16, the rotating frame 17, a control device 18, and a gantry driving device 19. The X-ray tube 11, the wedge 12, the collimator 13, the X-ray high voltage device 14, the X-ray detector 15, the DAS 16, the rotating frame 17, and the control device 18 are housed in a housing. The housing is provided with input interfaces such as switches that are operated by an operator. The rotating frame 17 rotatably holds the X-ray tube 11, the wedge 12, the collimator 13, and the X-ray detector 15. The rotating frame 17 may hold the X-ray detector 15, the DAS 16, and the control device 18.

The X-ray tube 11 generates X-rays by radiating thermo-electrons from the cathode (filament) toward the anode (target) when a high voltage from the X-ray high voltage device 14 is applied thereto. The X-ray tube 11 includes a vacuum tube. For example, the X-ray tube 11 is a rotating anode type X-ray tube that generates X-rays by radiating thermoelectrons to a rotating anode.

The wedge 12 is a filter for adjusting the X-ray dose radiated from the X-ray tube 11 to a subject P. The wedge 12 attenuates the X-rays that pass through the wedge 12 such that the distribution of the X-ray dose radiated from the X-ray tube 11 to the subject P becomes a predetermined distribution. The wedge 12 is also called a wedge filter or a bow-tie filter. The wedge 12 is, for example, made of aluminum processed to have a predetermined target angle and a predetermined thickness.

The collimator 13 is a mechanism for narrowing down the radiation range of X-rays that have passed through the wedge 12. The collimator 13 narrows down the radiation range of X-rays by forming a slit using a combination of a plurality of lead plates, for example. The collimator 13 may be called an X-ray diaphragm. The narrowing range of the collimator 13 may be mechanically drivable.

The X-ray high voltage device 14 includes, for example, a high voltage generator that is not shown and an X-ray control device that is not shown. The high voltage generator has an electric circuit including a transformer, a rectifier, and the like, and generates a high voltage to be applied to the X-ray tube 11. The X-ray control device controls an output voltage of the high voltage generator depending on the X-ray dose to be generated in the X-ray tube 11. The high voltage generator may boost a voltage using the aforementioned transformer or may boost a voltage using an inverter. The X-ray high voltage device 14 may be provided on the rotating frame 17 or may be provided on the side of a fixed frame (not shown) of the gantry 10.

The X-ray detector 15 detects the intensity of X-rays generated by the X-ray tube 11 and incident thereon after having passed through the subject P. The X-ray detector 15 outputs an electrical signal (may output an optical signal or the like) corresponding to the detected intensity of X-rays to the DAS 16. The X-ray detector 15 has, for example, a plurality of X-ray detection element rows. Each of the plurality of X-ray detection element rows has a plurality of X-ray detection elements arranged in a channel direction along an arc having the focal point of the X-ray tube 11 as the center. The plurality of X-ray detection element rows are arranged in a slice direction (row direction).

In the X-ray detector 15, unless the area for detecting one unit of X-ray photons is spatially narrowed, if a plurality of X-ray photons enter one X-ray detection element at the same time, it may become difficult to distinguish between a single photon with high energy and two photons with low energy. On the other hand, with one subpixel, the area is excessively small and a detection signal is excessively small, and thus a sufficient signal value may not be obtained due to S/N problems. For this reason, one X-ray detection element is formed by bundling a plurality of sub-pixels, for example 3×3 subpixels.

The X-ray detector 15 is, for example, a direct detection type detector. As the X-ray detector 15, for example, a semiconductor diode having electrodes attached to both ends of a semiconductor can be applied. X-ray photons incident on a semiconductor are converted into electron-hole pairs. The number of electron-hole pairs generated by the incidence of one X-ray photon depends on the energy of the incident X-ray photon. Electrons and holes are attracted to a pair of electrodes formed at both ends of the semiconductor. The pair of electrodes generates an electric pulse having a pulse height value depending on the charge of the electron-hole pairs. One electric pulse has a pulse height value corresponding to the energy of the incident X-ray photon. X-ray photons are an example of a material.

The DAS 16 collects count data indicating the number of counts of X-ray photons detected by the X-ray detector 15 with respect to a plurality of energy bins, for example, according to a control signal from the control device 18. The count data regarding the plurality of energy bins corresponds to the energy spectrum regarding X-rays incident on the X-ray detector 15, which has been modified according to the response characteristics of the X-ray detector 15. The DAS 16 outputs detection data based on digital signals to control device 18. The detection data is a digital value of count data identified by the channel number and the row number of an X-ray detection element that is a generation source, and the view number indicating a collected view. The view number is a number that changes according to rotation of the rotating frame 17 and is a number that increments according to rotation of the rotating frame 17, for example. Therefore, the view number is information indicating the rotation angle of the X-ray tube 11. A view period is a period that falls between a rotation angle corresponding to a certain view number and a rotation angle corresponding to the next view number. The DAS 16 may detect switching of views using a timing signal input from the control device 18, an internal timer, or a signal obtained from a sensor that is not shown. In a case where the X-ray tube 11 continuously emits X-rays during full scanning, the DAS 16 collects a detection data group for the entire circumference (360 degrees). In a case where the X-ray tube 11 continuously emits X-rays during half scanning, the DAS 16 collects detection data for half the circumference (180 degrees).

Figure 2:
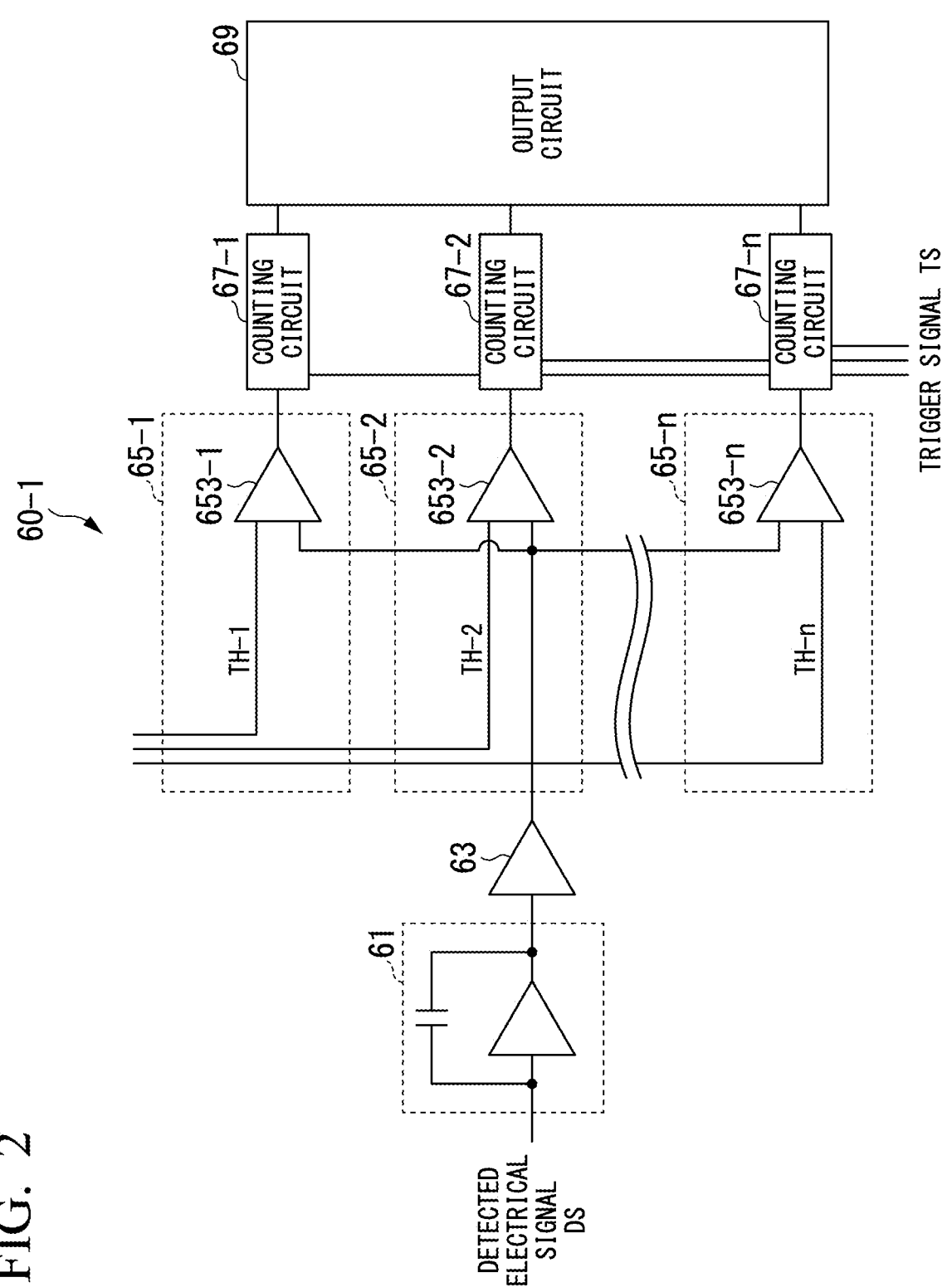
FIG. 2 is a diagram showing an example of a configuration of a DAS 16 according to the first embodiment.

FIG. 2 is a diagram showing an example of the configuration of the DAS 16 according to the first embodiment. The DAS 16 includes readout channels corresponding to the number of X-ray detection elements. These plurality of readout channels are mounted in parallel in an integrated circuit such as an application specific integrated circuit (ASIC) or the like. FIG. 2 shows only the configuration of a DAS 16-1 for one read channel.

The DAS 16-1 includes a preamplifier circuit 61, a waveform shaping circuit 63, a plurality of pulse height distinguishment circuits 65, a plurality of counting circuits 67, and an output circuit 69. The preamplifier circuit 61 amplifies a detected electrical signal DS (current signal) from a connected X-ray detection element. For example, the preamplifier circuit 61 converts the current signal from the connected X-ray detection element into a voltage signal having a voltage value (pulse height value) proportional to the amount of charge of the current signal. The waveform shaping circuit 63 is connected to the preamplifier circuit 61. The waveform shaping circuit 63 shapes the waveform of the voltage signal from the preamplifier circuit 61. For example, the waveform shaping circuit 63 reduces the pulse width of the voltage signal from the preamplifier circuit 61.

A plurality of counting channels corresponding to the number of energy bands (energy bins) are connected to the waveform shaping circuit 63. In a case in which n energy bins are set, the waveform shaping circuit 63 is provided with n counting channels. Each counting channel has a pulse height distinguishment circuit 65-$n$ and a counting circuit 67-$n$.

Each of the pulse height distinguishment circuits 65-$n$ distinguish the energy of X-ray photons detected by the X-ray detection element, which is the pulse height value of the voltage signal from the waveform shaping circuit 63. For example, the pulse height distinguishment circuits 65-$n$ include comparison circuits 653-$n$. The voltage signal from the waveform shaping circuit 63 is input to one input terminal of each of the comparison circuits 653-$n$. Reference signals TH (reference voltage values) corresponding to different threshold values are supplied from the control device 18 to the other input terminals of the comparison circuits 653-$n$. For example, a reference signal TH-1 is supplied to the comparison circuit 653-1 for an energy bin bin1, a reference signal TH-2 is supplied to the comparison circuit 653-2 for an energy bin bin2, and a reference signal TH-$n$ is supplied to the comparison circuit 653-$n$ for an energy bin binn. Each of the reference signals TH has an upper limit reference value and a lower limit reference value. Each of the comparison circuits 653-$n$ outputs an electric pulse signal in a case in which the voltage signal from the waveform shaping circuit 63 has a pulse height value corresponding to the energy bin corresponding to each of the reference signals TH. For example, the comparison circuit 653-1 outputs an electrical pulse signal in a case in which the pulse height value of the voltage signal from the waveform shaping circuit 63 corresponds to energy bin bin1 (in a case in which the pulse height value falls between the reference signals TH-1 and TH-2). On the other hand, the comparison circuit 653-1 for the energy bin bin1 does not output an electric pulse signal in a case in which the pulse height value of the voltage signal from the waveform shaping circuit 63 does not correspond to the energy bin bin1. Further, for example, the comparison circuit 653-2 outputs an electrical pulse signal in a case in which the pulse height value of the voltage signal from the waveform shaping circuit 63 corresponds to the energy bin bin2 (in a case in which the pulse height value falls between the reference signals TH-2 and TH-3).

The counting circuits 67-$n$ count the electrical pulse signals from the pulse height distinguishment circuits 65-$n$ at a readout cycle that matches a view switching cycle. For example, a trigger signal TS is supplied from the control device 18 to the counting circuits 67-$n$ at a switching timing of each view. By being triggered by supply of the trigger signal TS, the counting circuits 67-$n$ add 1 to counts stored in internal memories every time electric pulse signals are input from the pulse height distinguishment circuits 65-$n$. By being triggered by supply of the next trigger signal, the counting circuits 67-$n$ read count number data (i.e., count data) accumulated in the internal memories and supply the count data to the output circuit 69. In addition, the counting circuits 67-$n$ reset the counts stored in the internal memories to an initial value every time the trigger signal TS is supplied. In this manner, the counting circuits 67-$n$ count a count number for each view.

The output circuit 69 is connected to counting circuits 67-$n$ corresponding to a plurality of readout channels mounted in the X-ray detector 15. For each of the plurality of energy bins, the output circuit 69 integrates count data from the counting circuits 67-$n$ corresponding to the plurality of readout channels to generate count data corresponding to the plurality of readout channels for each view. Count data of each energy bin is a set of count number data defined by a channel, a segment (row), and an energy bin. The count data of each energy bin is transmitted to the console device 40 in units of views. Count data in units of views is called a count data set CS.

Referring back to FIG. 1, the rotating frame 17 is an annular member that supports the X-ray tube 11, the wedge 12, the collimator 13, and the X-ray detector 15 in a facing manner. The rotating frame 17 is rotatably supported by a fixed frame around a subject P introduced therein. The rotating frame 17 further supports the DAS 16. Detection data output from the DAS 16 is transmitted through optical communication from a transmitter having a light emitting diode (LED) provided in the rotating frame 17 to a receiver having a photodiode provided in a non-rotating part (for example, a fixed frame) of the gantry 10 and transferred by the receiver to the console device 40. Note that the method of transmitting detection data from the rotating frame 17 to the non-rotating part is not limited to the method using optical communication described above, and any contactless transmission method may be employed. The rotating frame 17 is not limited to an annular member and may be a member such as an arm as long as it can support and rotate the X-ray tube 11 and the like.

Although the X-ray CT apparatus 1 is, for example, a Rotate/Rotate-Type X-ray CT apparatus (a third generation CT) in which both the X-ray tube 11 and the X-ray detector 15 are supported by the rotating frame 17 and rotate around the subject P, the X-ray CT apparatus 1 is not limited thereto and may be a Stationary/Rotate-Type X-ray CT apparatus (fourth generation CT) in which a plurality of X-ray detection elements arranged in an annular shape are fixed to a fixed frame and the X-ray tube 11 rotates around the subject P.

The control device 18 includes, for example, processing circuitry having a processor such as a CPU. The control device 18 receives an input signal from an input interface attached to the gantry 10 or the console device 40 and controls the operations of the gantry 10, the bed device 30, and the DAS 16. For example, the control device 18 controls the gantry driving device 19 to rotate the rotating frame 17 or tilt the gantry 10. At the time of tilting the gantry 10, the control device 18 controls the gantry driving device 19 on the basis of an inclination angle (tilt angle) input to the input interface to rotate the rotating frame 17 around an axis parallel to the Z-axis direction. The control device 18 ascertains the rotation angle of the rotating frame 17 on the basis of the output of a sensor that is not shown, or the like. Further, the control device 18 provides the rotation angle of the rotating frame 17 to a reconstruction function 53 and the like at any time. Further, the control device 18 controls the energy bins (reference signal TH) of the DAS 16. The control device 18 may be provided in the gantry 10 or may be provided in the console device 40.

Figure 3:
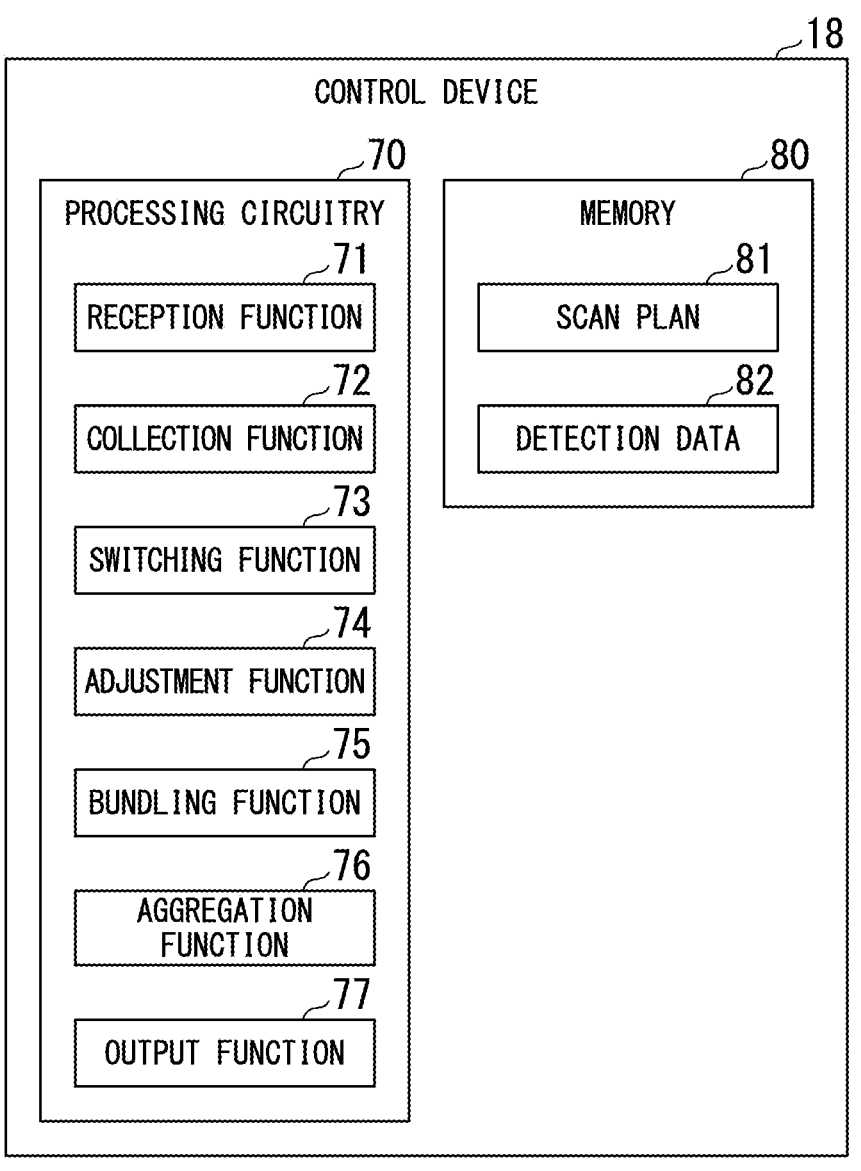
FIG. 3 is a diagram showing an example of a part of the configuration of a control device 18 according to the first embodiment.

The control device 18 distinguishes and collects detection data output by the DAS 16, outputs the collected detection data to the console device 40, or stores the detection data in a storage device. FIG. 3 is a diagram showing an example of a part of the configuration of the control device 18 according to the first embodiment. FIG. 3 shows configurations of processing circuitry 70 and a memory 80 related to a function of controlling the DAS 16 in the control device 18.

The processing circuitry 70 includes, for example, a reception function 71, a collection function 72, a switching function 73, an adjustment function 74, a bundling function 75, an aggregation function 76, and an output function 77. Such components of the processing circuitry 70 are realized, for example, by a hardware processor (computer) executing a program (software) stored in a memory 41, for example. The hardware processor is, for example, circuitry such as a CPU, a graphics processing unit (GPU), an application specific integrated circuit (ASIC), or a programmable logic device (for example, a simple programmable logic device (SPLD), a complex programmable logic device (CPLD), or a field programmable gate array (FPGA)). The program may be directly incorporated into the circuitry of the hardware processor instead of being stored in the memory 41. In this case, the hardware processor realizes the functions thereof by reading and executing the program incorporated into the circuitry. The hardware processor is not limited to being configured as a single circuit, and may be configured as one hardware processor by combining a plurality of independent circuits to realize each function. Further, a plurality of components may be integrated into one hardware processor to realize each function.

The reception function 71 receives various types of information transmitted from the input interface provided in the gantry 10 or the console device 40. The information transmitted by the input interface or the console device 40 includes, for example, information regarding a scan plan, information regarding various settings with respect to energy bins, and detection data request information for requesting detection data. For example, the reception function 71 stores received information, such as a scan plan 81, in the memory 80.

The collection function 72 collects detection data that is data corresponding to the energy of a material, such as an X-ray photon. The collection function 72 collects, for example, detection data output by the DAS 16 as detection data. The collection function 72 stores collected detection data 82 in the memory 80. The collection function 72 is an example of a collector.

The switching function 73 switches collection modes for collecting data between a first mode and a second mode. The collection modes are, for example, common to operation modes of the X-ray CT apparatus 1. Among the operating modes of the X-ray CT apparatus 1, the first mode is a mode used, for example, in CT fluoroscopy and real prep, which require real-time performance (time responsiveness) rather than image accuracy, and is a mode in which the amount of data transmitted in real time is limited by the output function 77. The second mode is a mode used, for example, during surgery and the like in which accuracy is required rather than real-time performance of images, and is a mode in which the amount of data transmitted in real time is not limited by the output function 77 or is limited to a small amount is limited. Note that real time means that when times exactly match, a deviation is allowed for a delay time that varies depending on other purposes. The collection function 72 stores detection data 82 in the memory 80, for example, in the first mode. The switching function 73 is an example of a switcher.

Among the collection modes, the first mode is, for example, a mode in which the number of energy bins is set to a small number, for example, only a single number (one), and the number of X-ray photons is counted based on numerical criteria (range of pulse height values) in which one energy bin is wide. The number of energy bins set in the first mode may be less than the number of energy bins set in the second mode, and may be plural.

Among the collection modes, the second mode is a mode in which a large number of energy bins are set and the number of X-ray photons is counted using energy bins that are finely divided based on narrow numerical criteria. The switching function 73 may switch the collection mode on the basis of, for example, mode setting information transmitted by the input interface or the console device 40 or mode setting information included in the scan plan.

The adjustment function 74 adjusts conditions for detection data when the detection data is collected on the basis of the collection mode switched by the switching function 73. The conditions for detection data is, for example, the number of energy bins for distinguishing the detection data detected by the DAS 16. The adjustment function 74 adjusts the number of energy bins to a number depending on the collection mode. The adjustment function 74 is an example of an adjuster.

The number of energy bins in the DAS 16 is determined, for example, on the basis of the energy band of X-ray to be detected and the distinguishing performance thereof, and can be set to a large number such as 10 or more (hereinafter, a first maximum value) in theory. On the other hand, even if the distinguishing performance is improved and the energy bins are set finely, the resolution of the X-ray detector 15 may not be guaranteed, and in this case, the significance of setting the fine energy bins becomes small. Therefore, the number of energy bins that can be used clinically as a device may be, for example, 5 or 6 (hereinafter, a second maximum value).

Based on the idea of the first maximum value and the second maximum value, the adjustment function 74 sets the number of energy bins to a number less than the second maximum value in the first mode in a case in which the number of energy bins in the second mode has been set to the second maximum value, for example. In a case in which the number of energy bins in the second mode has been set to the second maximum value, for example, the adjustment function 74 may set the number of energy bins to a number less than the second maximum value in the first mode. The first mode of the first embodiment is a mode in which one energy bin is set, and thus the number of X-ray photons in energy bands that can be detected in the second mode is all counted in one energy bin.

For example, the adjustment function 74 may adjust the number of energy bins by adjusting numerical criteria regarding energy at the time of distinguishing detection data. The numerical criteria regarding energy are, for example, the range of pulse height values when data is distinguished using energy bins. The numerical criteria are set in advance for each of the first mode and the second mode. The numerical criteria may be changeable (adjustable) based on information transmitted by the input interface or the console device 40.

The bundling function 75 bundles detection data distinguished with some of the plurality of energy bins. Which energy bins by which detection data to be grouped is distinguished may be determined based on, for example, mode setting information transmitted by the input interface or the console device 40 or mode setting information included in a scan plan. The bundling function 75 is an example of a bundler.

The aggregation function 76 aggregates the detection data bundled by the bundling function 75. The aggregation function 76 aggregates the detection data by adding count data according to the bundled detection data. In the following description, processing of bundling detection data by the bundling function 75 and processing of aggregating detection data bundled by the bundling function 75 will be referred to as post-DAS bundling processing. The aggregation function 76 is an example of an aggregator.

When the number of energy bins is set to one in the first mode, detection data is not bundled by the bundling function 75. In this case, the aggregation function 76 aggregates count data included in one energy bin as an aggregate of detection data as it is. In the following description, processing in which count data included in one energy bin is used as an aggregate of detected data as it is referred to as pre-DAS bundling processing.

Note that, in a case in which a plurality of energy bins are set in the first mode, the pre-DAS bundling process includes processing of bundling detection data by the bundling function 75 and processing of aggregating detection data bundled by the bundling function 75, similar to the post-DAS bundling processing. In this case, the number of energy bins at the time of performing the pre-DAS bundling processing is adjusted to be less than the number of energy bins at the time of performing the post-DAS bundling processing.

Therefore, the number of pieces of detection data aggregated through the pre-DAS bundling processing becomes less than the number of pieces of detection data aggregated through the post-DAS bundling processing. Therefore, the load on the control device 18 and the amount of data transmitted from the control device 18 to the console device 40 in the pre-DAS bundling processing are less (lighter) than those in the post-DAS bundling processing.

When the switching function 73 switches the collection mode, the aggregation function 76 switches between pre-DAS bundling processing and the post-DAS bundling processing, and thus the switching function 73 substantially switches between the pre-DAS bundling processing and the post-DAS bundling processing. Although the switching function 73 switches between the pre-DAS bundling processing and the post-DAS bundling processing by switching the collection mode in the first embodiment, it may be possible to switch between the pre-DAS bundling processing and the post-DAS bundling processing in a manner different from the manner in which the collection mode is switched.

The output function 77 outputs the detection data aggregated by the aggregation function 76 by transmitting the detection data to the console device 40. For example, the output function 77 outputs detection data stored in the memory 80 after outputting the detection data aggregated by the aggregation function 76. The output function 77 is an example of an output.

Each function included in the processing circuitry 70 may be provided in circuitry independent from the control device 18 that controls the operations of the gantry 10, the bed device 30, and the DAS 16 within the gantry 10. For example, each function included in the processing circuitry 70 may be provided in association with the DAS 16.

The memory 80 is realized by, for example, a random access memory (RAM), a semiconductor memory element such as a flash memory, a hard disk, an optical disk, or the like. The memory 80 stores a scan plan 81 transmitted by the console device 40 and received by the reception function 71, detection data 82 aggregated by the aggregation function 76, and the like. The scan plan 81 stored in the memory 80 is updated every time the console device 40 transmits a scan plan. The detection data 82 stored in the memory 80 is transmitted to an external device or like, for example, in a case in which further analysis or the like of an image is required in the external device such as the console device 40 after scanning of a subject is completed. The memory 80 is an example of a buffer.

Referring back to FIG. 1, the gantry driving device 19 includes, for example, a motor and an actuator. The gantry driving device 19 rotates the rotating frame 17 or tilts the gantry 10, for example. The gantry driving device 19 rotates the rotating frame 17 of the gantry 10 on the basis of an inclination angle (tilt angle) input to the input interface and a rotation instruction from a correction data collection function 57 which will be described later.

The bed device 30 is a device that moves the to-be-scanned subject P placed thereon to introduce the patient P into the rotating frame 17 of the gantry 10. The bed device 30 includes, for example, a base 31, a bed driving device 32, a top plate 33, and a support frame 34. The base 31 includes a housing that supports the support frame 34 such that the support frame 24 can move in the vertical direction (Y-axis direction). The bed driving device 32 includes a motor and an actuator. The bed driving device 32 moves the top plate 33 along the support frame 34 in the longitudinal direction of the top plate 33 (Z-axis direction). Further, the bed driving device 32 moves the top plate 33 in the vertical direction (Y-axis direction). The top plate 33 is a plate-shaped member on which the subject P is placed.

The bed driving device 32 may move not only the top plate 33 but also the support frame 34 in the longitudinal direction of the top plate 33. Further, contrary to the above, the gantry 10 may be movable in the Z-axis direction, and the rotating frame 17 may be controlled to come around the subject P according to movement of the gantry 10. Further, both the gantry 10 and the top plate 33 may be movable. In addition, the X-ray CT apparatus 1 may be an apparatus in which the subject P is scanned in a standing or sitting position. In this case, the X-ray CT apparatus 1 includes a subject support mechanism instead of the bed device 30, and the gantry 10 rotates the rotating frame 17 about an axial direction perpendicular to the floor surface.

The console device 40 includes, for example, a memory 41, a display 42, an input interface 43, and processing circuitry 50. Although the console device 40 is described as being separate from the gantry 10 in the first embodiment, the gantry 10 may include some or all of the components of the console device 40.

The memory 41 is realized by, for example, a semiconductor element such as a random access memory (RAM) or a flash memory, a hard disk, an optical disk, or the like. The memory 41 stores, for example, detection data, projection data, reconstructed image data, CT image data, information on the subject P, imaging conditions, correction data collection conditions, and the like. The memory 41 stores, for example, count data regarding a plurality of energy bins transmitted from the gantry 10. Such data may be stored in an external memory with which the X-ray CT apparatus 1 can communicate instead of the memory 41 (or in addition to the memory 41). The external memory is controlled by a cloud server managing the external memory, for example, when the cloud server receives read/write requests.

The display 42 displays various types of information. For example, the display 42 displays medical images (CT images) generated by processing circuitry, graphical user interface (GUI) images through which various operations performed by an operator such as a doctor or a technician are received, and the like. The display 42 is, for example, a liquid crystal display, a cathode ray tube (CRT), an organic electroluminescence (EL) display, or the like. The display 42 may be provided on the gantry 10. The display 42 may be of a desktop type or may be a display device (for example, a tablet terminal) that can communicate wirelessly with the main body of the console device 40.

The input interface 43 receives various input operations performed by an operator and outputs an electrical signal indicating details of the received input operations to the processing circuitry 50. For example, the input interface 43 receives operations of inputting mode setting information indicating a mode to be set (first mode or second mode), scan plan transmission instruction information for instructing transmission of a scan plan, and detection data request information for requesting detection data. The console device 40 transmits a scan plan to the control device 18 when the input interface 43 receives an input operation for scan plan transmission instruction information. The console device 40 transmits the detection data request information to the control device 18 when the input interface 43 receives an input operation for the detection data request information.

For example, the input interface 43 is realized by a mouse, a keyboard, a touch panel, a track ball, a switch, a button, a joystick, a camera, an infrared sensor, a microphone, or the like. The input interface 43 may be provided in the gantry 10. Further, the input interface 43 may be realized by a display device (for example, a tablet terminal) that can communicate wirelessly with the main body of the console device 40.

Note that in this specification, the input interface is not limited to one that includes physical operation parts such as a mouse and a keyboard. For example, examples of the input interface also include electrical signal processing circuitry that receives an electrical signal corresponding to an input operation from external input equipment provided separately from the apparatus and outputs this electrical signal to a control circuit.

The processing circuitry 50 controls the overall operation of the X-ray CT apparatus 1, the operation of the gantry 10, the operation of the bed device 30, and a calibration operation for collecting correction data. The processing circuitry 50 includes, for example, a system control function 51, a preprocessing function 52, a reconstruction function 53, an image processing function 54, and the like.

These components are realized, for example, by a hardware processor (computer) executing a program (software) stored in the memory 41. The hardware processor is, for example, circuitry such as a CPU, a graphics processing unit (GPU), an application specific integrated circuit (ASIC), or a programmable logic device (for example, a simple programmable logic device (SPLD), a complex programmable logic device (CPLD), or a field programmable gate array (FPGA). The program may be directly incorporated into the circuitry of the hardware processor instead of being stored in the memory 41.

In this case, the hardware processor realizes the functions by reading and executing the program incorporated into the circuitry. The hardware processor is not limited to being configured as a single circuit and may be configured as one hardware processor by combining a plurality of independent circuits to realize each function. Further, a plurality of components may be integrated into one hardware processor to realize each function.

The respective components included in the console device 40 or the processing circuitry 50 may be distributed and realized by a plurality of pieces of hardware. The processing circuitry 50 may be realized by a processing device that can communicate with the console device 40 instead of being a component included in the console device 40. The processing device is, for example, a workstation connected to one X-ray CT apparatus, or a device (e.g., a cloud server) that is connected to a plurality of X-ray CT apparatuses and collectively executes the same processing as that of the processing circuitry 50 which will be described below.

The system control function 51 controls various functions of the processing circuitry 50 on the basis of input operations received by the input interface 43.

The preprocessing function 52 performs preprocessing such as logarithmic conversion processing, offset correction processing, inter-channel sensitivity correction processing, beam hardening correction, scattered radiation correction, and dark count correction on detection data output by the DAS 16 to generate projection data. The projection data includes count data.

The reconstruction function 53 reconstructs a photon counting type CT image of the subject P on the basis of detection data (count data). FIG. 4 is a diagram showing an example of functional blocks of the reconstruction function 53 according to the first embodiment. The reconstruction function 53 includes, for example, a response function generation function 531, an X-ray absorption amount calculation function 532, and a reconstruction processing function 533. The response function generation function 531 generates response function data representing detector response characteristics. For example, the response function generation function 531 measures a response (i.e., detected energy and detected intensity) of a standard detection system to a plurality of monochromatic X-rays having a plurality of incident X-ray energies according to predictive calculation, experiment, and a combination of predictive calculation and experiment, and generates a response function on the basis of the measured values of detected energy and detected intensity. Further, the response function generation function 531 may generate response function data on the basis of actual measurement values collected during calibration or the like. A response function defines the relationship between a detected energy for each incident x-ray and an output response of the system. For example, the response function defines the relationship between a detected energy and a detected intensity for each incident X-ray. The generated response function data is stored in the memory 41.

The X-ray absorption amount calculation function 532 calculates an X-ray absorption amount for each of a plurality of base materials on the basis of count data regarding a plurality of energy bins, the energy spectrum of X-rays incident on the subject P, and the response function stored in the memory 41. The X-ray absorption amount calculation function 532 can calculate an X-ray absorption amount that is not affected by the response characteristics of the X-ray detector 15 and the DAS 16 by calculating the X-ray absorption amount on the basis of the count data and the energy spectrum of the X-rays incident on the subject P using the response function. Processing of obtaining the X-ray absorption amount for each base material in this manner is also called material distinguishment. Base materials can be set to any material such as calcium, calcification, bone, fat, muscle, air, organ, lesion, hard tissue, soft tissue, and contrast material. The type of base material to be calculated may be determined in advance by an operator or the like via the input interface 43. An X-ray absorption amount indicates the amount of X-rays absorbed by a base material. For example, an X-ray absorption amount is defined by a combination of an X-ray attenuation coefficient and an X-ray transmission path length.

The reconstruction processing function 533 reconstructs a photon counting type CT image representing a spatial distribution of a base material to be imaged among a plurality of base materials on the basis of the X-ray absorption amount for each of the plurality of base materials calculated by the X-ray absorption amount calculation function 532 and causes generated CT image data to be stored in the memory 41. The base material to be imaged may be one type of base material or a plurality of types of base materials. The type of base material to be imaged may be determined by an operator or the like via the input interface 43.

Projection data including count data obtained by the photon counting CT apparatus includes information on the energy of X-rays attenuated by passing through the subject P. Therefore, the reconstruction processing function 533 can reconstruct CT image data of a specific energy component, for example. Furthermore, the reconstruction processing function 533 can reconstruct CT image data of each of a plurality of energy components, for example. Furthermore, the reconstruction processing function 533 can assign a color tone depending on each energy component to each pixel of the CT image data of each energy component, and generate image data in which a plurality of pieces of CT image data color-coded according to the energy components are superimposed.

Referring back to FIG. 1, the image processing function 54 generates a CT image on the basis of CT image data. The image processing function 54 causes the display 42 to display the generated CT image. The image processing function 54 acquires information regarding an inflow state of a contrast material flowing into a target organ of the subject P. The image processing function 54 causes the display 42 to display the generated inflow state information.

According to the above-described configuration, the X-ray CT apparatus 1 scans the subject P in a scanning manner such as helical scanning, conventional scanning, or step-and-shoot. Helical scanning is a mode in which the subject P is scanned in a spiral manner by rotating the rotating frame 17 while moving the top plate 33. Conventional scanning is a mode in which the rotating frame 17 is rotated while the top plate 33 is kept stationary to scan the subject P in a circular orbit. Step-and-shoot is a mode in which the position of the top plate 33 is moved at regular intervals to perform conventional scanning in a plurality of scanning areas.

Figure 5:
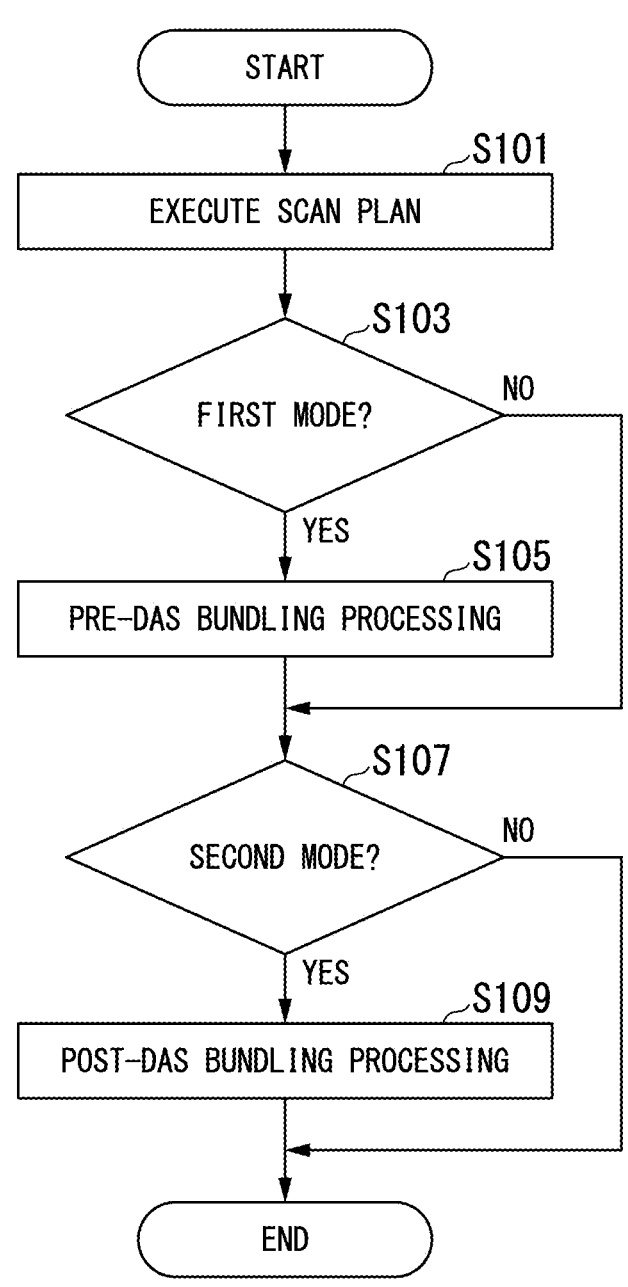
FIG. 5 is a flowchart showing an example of processing in the X-ray CT apparatus 1 according to the first embodiment.

Next, processing in the X-ray CT apparatus 1 according to the first embodiment will be described. FIG. 5 is a flowchart showing an example of processing in the X-ray CT apparatus 1 according to the first embodiment. In the X-ray CT apparatus 1 of the first embodiment, the control device 18 first executes the scan plan 81 stored in the memory 80 (step S101). Subsequently, the control device 18 determines whether or not the operation mode of the X-ray CT apparatus 1 is the first mode in the scan plan being executed (step S103).

In a case in which it is determined that the operation mode of the X-ray CT apparatus 1 is the first mode, the control device 18 performs pre-DAS bundling processing through the aggregation function 76 (step S105). When performing the DAS pre-bundling processing through the aggregation function 76, the control device 18 adjusts the number of energy bins to 1 and adjust numerical criteria to a full pulse height value through the adjustment function 74. In a case in which it is determined in step S103 that the operation mode of the X-ray CT apparatus 1 is not the first mode, the control device 18 causes processing to proceed to step S105.

Subsequently, the control device 18 determines whether the operation mode of the X-ray CT apparatus 1 has been switched from the first mode to the second mode, and the collection mode has been switched from the first mode to the second mode through the switching function 73 (step S107). In a case in which it is determined that the collection mode has been switched from the first mode to the second mode through the switching function 73, the control device 18 performs post-DAS bundling processing through the aggregation function 76 (step S109).

When performing the post-DAS bundling processing through the aggregation function 76, the control device 18 adjusts the number of energy bins to a predetermined number greater than 1 and adjusts a pulse height value indicating numerical criteria for each energy bin through the adjustment function 74. The number of energy bins at the time of performing the post-DAS bundling processing through the aggregation function 76 may be, for example, a maximum number of energy bins that can be adjusted by the adjustment function 74, or a number of energy bins that is less than the maximum number of energy bins.

When the number of energy bins increases, the number of pieces of detection data output by the output function 77 increases accordingly. Since a transmission capacity is limited by the control device 18, when the number of pieces of detection data to be output increases, it takes a time to transmit the detection data. As a result, in processing that requires real-time performance, for example, a maximum number of energy bins may be determined within a range in which the required real-time performance can be maintained.

The numerical criteria in the energy bins may be adjusted in any manner. For example, the numerical criteria may be determined in advance in association with the number of energy bins to be adjusted, and when adjustment of the number of energy bins is completed, adjustment of the numerical criteria for the energy bins may also be completed. In this manner, the control device 18 ends processing shown in FIG. 5.

The X-ray CT apparatus 1 of the first embodiment can perform post-DAS bundling processing. Therefore, the amount of data transmitted when real-time performance is required can be reduced. Further, the X-ray CT apparatus 1 of the first embodiment can also perform pre-DAS bundling processing and can switch between pre-DAS bundling processing and post-DAS bundling processing. Therefore, it is possible to fully utilize the advantage of counting the number of X-ray photons for each energy.

Further, the X-ray CT apparatus 1 of the first embodiment can store the detection data 82 in the memory 80. Accordingly, in situations in which real-time performance is required, it is possible to temporarily store collected detection data in the memory 80, and when the demand for real-time performance decreases, re-transmit the detection data to the console device 40, a workstation, or the like at the time of performing post-DAS bundling processing and transmitting detection data. Therefore, analysis using energy information can be subsequently performed.

Furthermore, since the X-ray CT apparatus 1 of the first embodiment performs pre-DAS bundling processing and post-DAS bundling processing, it is possible to reduce the amount of data by reducing the amount of energy information or lowering energy resolution. Therefore, the X-ray CT apparatus 1 of the first embodiment can be suitably used in cases in which the degree of freedom of subsequent analysis is not required.

Although pre-DAS bundling processing is performed in the first mode and post-DS bundling processing is performed in the second mode in the first embodiment, post-DAS bundling processing (hereinafter, simple post-DAS bundling processing) may also be performed in the first mode if the number of energy bins in the first mode decreases. For example, it is assumed that first energy bin #1 to fourth energy bin #4 are set as energy bins. Further, it is assumed that detection data needs to be bundled into three bins due to the requirement for real-time transmission amount.

In this case, in the first mode, for example, pieces of detection data included in second energy bin #2 and third energy bin #3 may be bundled through simple post-DAS bundling processing to reduce the amount of data to be transmitted in processing that requires real-time performance. At the time of performing subsequent analysis, for example, in addition to the total of second energy bin #2 and third energy bin #3, the total of detection data of first energy bin #1 and fourth energy bin #4, detection data for three bins, is transmitted.

At this time, at the time of transmitting detection data subsequently, the detection data of first energy bin #1 and fourth energy bin #4 may be stored in the memory 80 during the first mode. Then, after scanning of the subject is completed and real-time performance is no longer required, post-DAS bundling processing may be performed and the detection data may be transmitted to the console device 40 or a workstation.

Further, in a case in which detection data bundled by the post-DAS bundling processing is transmitted to the console device 40, the detection data of first energy bin #1 and fourth energy bin #4 has already been transmitted. Therefore, in the post-DAS bundling processing, for example, it is only necessary to bundle and transmit the unbundled second energy bin #2 and third energy bin #3, and by transmitting such detected data, all of detection data used for analysis can be transmitted.

In addition, if the upper limit value of the transmission amount in real time is, for example, equivalent to three energy bins, pre-DAS bundling processing may be performed on the energy bins for 1 bin and 2 bins, or pre-DAS bundling processing may be performed for 2 bins in the first mode. In this case, if the upper limit value for the real-time transmission amount is not exceeded, for example, pre-DAS bundling processing may be performed for 3 bins without purposely performing pre-DAS bundling processing for 1 bin.

On the other hand, even if detection data is bundled by, for example, pre-DAS bundling processing, if the number of pieces of detection data increases, it is assumed that subsequent transmission (communication) and processing will take time. Therefore, the X-ray CT apparatus 1 may notify the operator or the like that all data can be transmitted in real time in the case of the number of energy bins which can ensure real-time performance through pre-DAS bundling processing. Further, in the case of the number of energy bins exceeding the real-time performance, the operator may be notified that some data will be transmitted subsequently.

Additionally, in a case in which the number of energy bins is set to a number less than the number that can ensure real-time performance before scanning according to a scan plan is started, additional bins may be provided. At the time of providing additional bins, the additional bins may be automatically provided, or the operator may be notified of a request for providing the additional bins. Even when additional bins are provided, threshold values may be maintained.

Second Embodiment

Next, an X-ray CT apparatus 1 of a second embodiment will be described. The X-ray CT apparatus of the second embodiment differs from the first embodiment mainly in that it includes an integration type CT circuit. In the following description, components common to those in the first embodiment may be denoted by the same reference numerals and the description thereof may be omitted.

Figure 6:
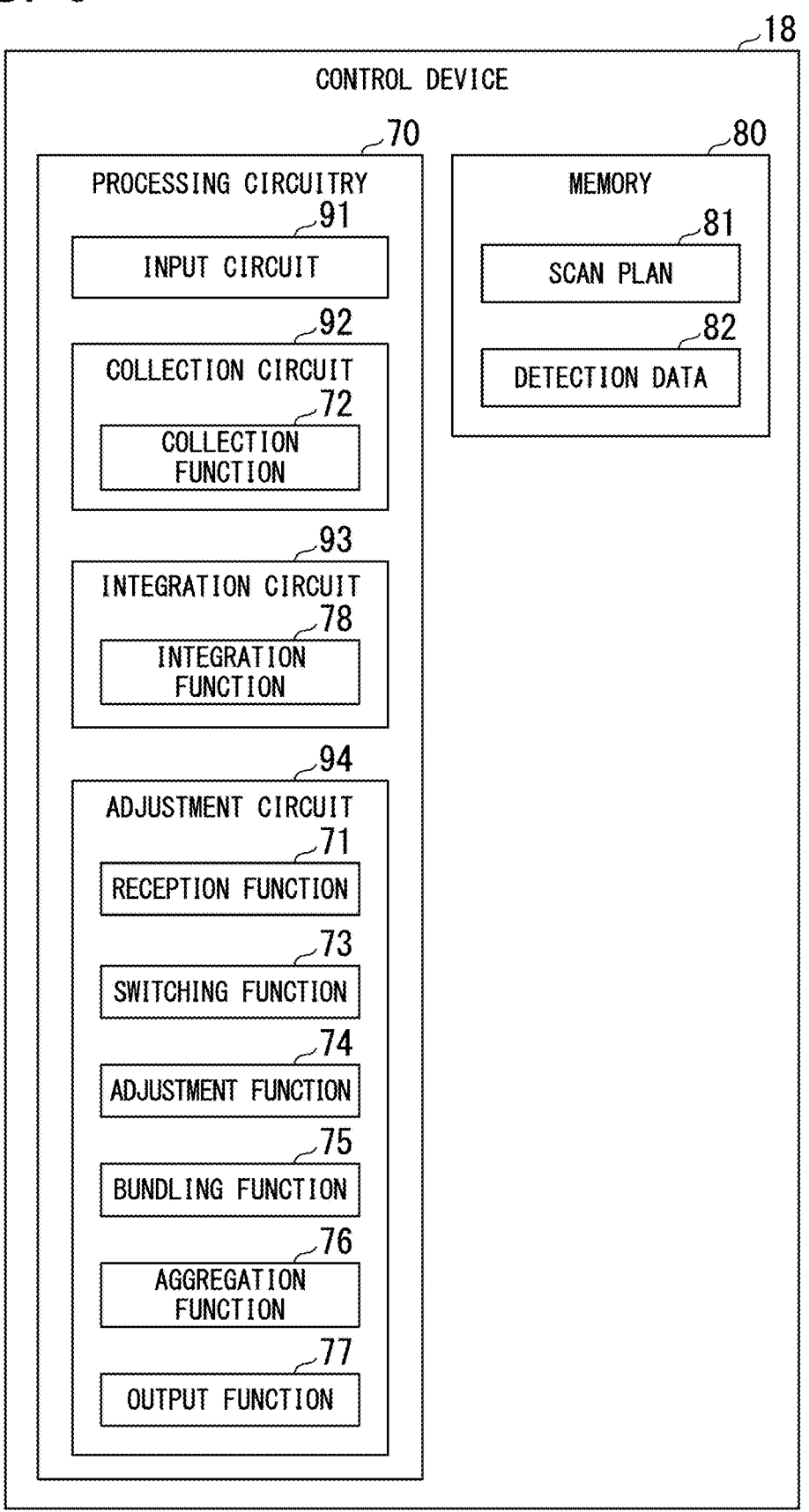
FIG. 6 is a diagram showing an example of a part of the configuration of the control device 18 according to a second embodiment.

FIG. 6 is a diagram showing an example of a part of the configuration of the control device 18 according to the second embodiment. The control device 18 according to the second embodiment also has the function of the DAS 16. The control device 18 includes the processing circuitry 70 and the memory 80 similarly to the first embodiment. The processing circuitry 70 includes an input circuit 91, a collection circuit 92, an integration circuit 93, and an adjustment circuit 94.

The input circuit 91 receives an electrical signal output by the X-ray detector 15 and outputs the electrical signal to the collection circuit 92 and the integration circuit 93. The collection circuit 92 is a so-called photon counting type CT circuit, and realizes the same function as the DAS 16 described in the first embodiment and the same function as the collection function 72 in the control device 18.

The integration circuit 93 is a so-called integration type CT circuit and realizes an integration function 78. The integration function 78 is an example of an integrator. The integration function 78 calculates integral data by integrating the energy of X-ray photons indicated by an electrical signal output by the X-ray detector 15 and generates the integral data as detection data. The adjustment circuit 94 realizes the reception function 71, the switching function 73, the adjustment function 74, the bundling function 75, the aggregation function 76, and the output function 77 in the first embodiment.

Among these, the switching function 73 switches the collection mode for collecting data between the first mode and the second mode, and as an energy integrating detector mode (hereinafter, an EID mode). For example, the EID mode is a mode in which real-time performance (time responsiveness) is required rather than image accuracy as in the first mode, but is a mode in which data with a higher detection strength of detected energy than in the first mode is required. The EID mode is an operation mode (collection mode) that is set when highly real-time processing is being performed, for example, during surgery. The aggregation function 76 generates detection data including values (hereinafter, CT values) related to voltage signals (integral data) accumulated in an integration type CT circuit, which will be described later. The EID mode is an example of a third mode.

Figure 7:
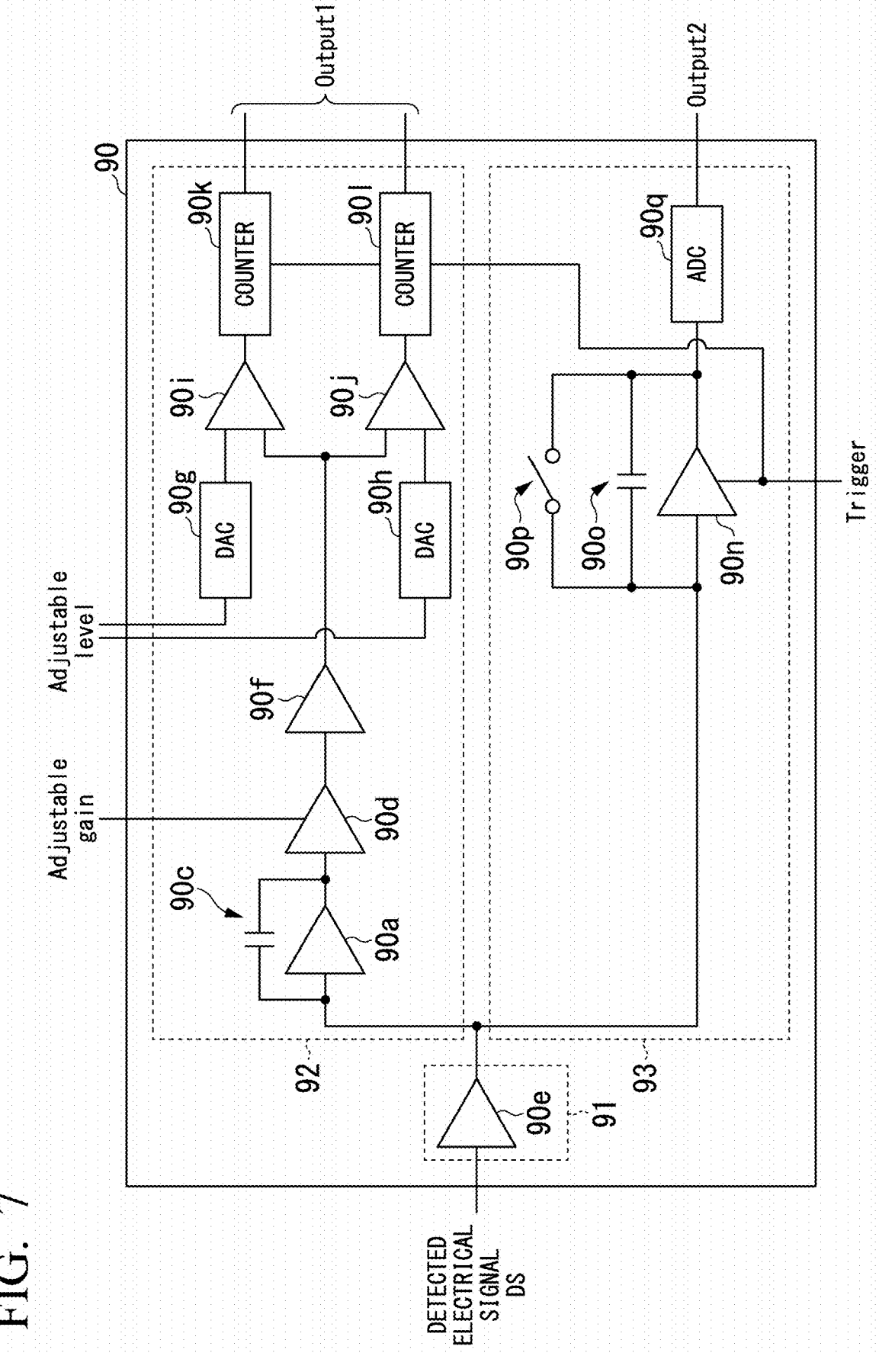
FIG. 7 is a diagram showing an example of a part of the configuration of processing circuitry 70 according to the second embodiment.

FIG. 7 is a diagram showing an example of a part of the configuration of the processing circuitry 90 according to the second embodiment. The processing circuitry 90 (a part of the processing circuitry 70) includes, for example, a preamplifier 90a, a capacitor 90c, an amplifier 90d, an amplifier 90e, a shaper 90f, a DAC 90g, a DAC 90h, a comparator 90i, a comparator 90j, a counter 90k, a counter 90l, an amplifier 90n, a capacitor 90o, a switch 90p, and an analog-to-digital converter (ADC) 90q.

In the processing circuitry 90, the amplifier 90e corresponds to the input circuit 91, the shaper 90f, the DAC 90g, the DAC 90h, the comparator 90i, the comparator 90j, the counter 90k, and the counter 90l correspond to the collection circuit 92, and the amplifier 90n, the capacitor 90o, the switch 90p, and the ADC 90q correspond to the integration circuit 93.

The preamplifier 90a and the capacitor 90c amplify pulses generated by a signal (charge pulses) output from the X-ray detector 15 and input to the processing circuitry 90. The amplifier 90d amplifies voltage pulses according to an adjustable gain. Note that the adjustable gain is arbitrarily set (adjusted) by an operation performed by the operator via the input interface or the console device 40. For example, the operator can set the adjustable gain as appropriate depending on variations in detector characteristics and an imaging mode.

The amplifier 90e corresponding to the input circuit 91 outputs current pulses to a circuit corresponding to the collection circuit 92 (photon counting type CT circuit) and a circuit corresponding to the integration circuit 93 (integration type CT circuit). For example, the amplifier 90e includes a current mirror circuit or a current conveyor circuit, duplicates input current pulses, and outputs the current pulses to the photon counting type CT circuit and the integration type CT circuit. That is, the amplifier 90e outputs the same current pulses to the photon counting type CT circuit and the integration type CT circuit.

The amplifier 90e can output weighted current pulses to the photon counting type CT circuit (the circuit corresponding to the collection circuit 92) and the integration type CT circuit (the circuit corresponding to the integration circuit 93). For example, in a case in which an optical sensor constituting a detector is an avalanche photodiode or a silicon photomultiplier, the sensor has a signal amplification mechanism inside thereof, and thus if a signal is output to the integration type CT circuit as it is, the integration type CT circuit will become saturated. Therefore, the amplifier 90e applies a weight to a signal to be output to the integration type CT circuit to reduce the signal. That is, if the weight for a signal to be output to the photon counting type CT circuit is set to "1," the amplifier 90e applies a weight of less than "1" to a signal to be output to the integration type CT circuit to reduce the signal to be output to the integration type CT circuit. Note that in a case in which the same current pulses are output, the amplifier 90e applies a weight of "1" to current pulses to be output to the photon counting type CT circuit and the integration type CT circuit.

Hereinafter, the photon counting type CT circuit will be described. The shaper 90f shapes the waveform of a voltage pulse output by the amplifier 90e and outputs the shaped voltage pulse to the comparator 90i and the comparator 90j. The DAC 90g and the DAC 90h convert an adjustable threshold value into an analog signal and output the analog signal to the comparator 90i and the comparator 90j. Note that the adjustable threshold value is arbitrarily level-adjusted by an operation performed by the operator via the input interface or the console device 40 (adjustable level).

The comparator 90i and the comparator 90j compare the threshold values input from the DAC 90g and the DAC 90h with the voltage pulses input from the shaper 90f, and when the intensity of the voltage pulses exceeds the threshold values, output electrical signals to the counters at the subsequent stage. The counter 90k and the counter 90l count the electrical signals output from the comparator 90i and the comparator 90j and output the counted values to the console device 40. The counter 90k and the counter 90l perform counting, output of counted values (Output1), and reset of counted values on the basis of an input trigger signal (Trigger). For example, the counter 90k and the counter 90l are controlled to output count data in synchronization with the rotation of the rotating frame 17 by outputting a trigger signal for each view.

Note that, although a case in which the processing circuitry 70 includes two DACs, comparators, and counters and collects count data of two energy bands (energy windows) has been illustrated, the embodiment is limited to thereto, and three or more DACs, comparators, and counters may be provided to collect count data of three or more energy bands (energy windows).

Next, the integration type CT circuit will be described. The amplifier 90n and the capacitor 90o amplify the voltage pulses output by amplifier 90e. The capacitor 90o accumulates the current pulses amplified by the amplifier 90e and outputs accumulated voltage signals (integral data) to the ADC 90q in response to ON/OFF switching by the switch 90p.

The switch 90p controls the output of integral data by the capacitor 90o by switching ON/OFF on the basis of a trigger signal (Trigger). The ADC 90q converts the received voltage signal (integral data) into a digital electrical signal and outputs the digital electrical signal (Output2). Note that, although a case in which the ADC 90q is provided in the processing circuitry 90 (in the integration circuit 93) is shown here, the present invention is not limited to thereto and the ADC 90q may be provided outside the processing circuitry 90, for example.

In the processing circuitry 70, the collection circuit 92 is connected to each X-ray detection element (pixel) in the X-ray detector 15, and photon counting type count data and integration type integral data are collected. Then, the processing circuitry 70 outputs (transmits) the collected count data and integral data to the console device 40 using the output function 77.

In the second embodiment, an example in which the processing circuitry 70 includes the collection circuit 92 and the integration circuit 93 configured in parallel has been described. On the other hand, the processing circuitry 70 may include the collection circuit 92 and the integration circuit 93 configured in series by disposing the integration circuit before the collection circuit 92.

Figure 8:
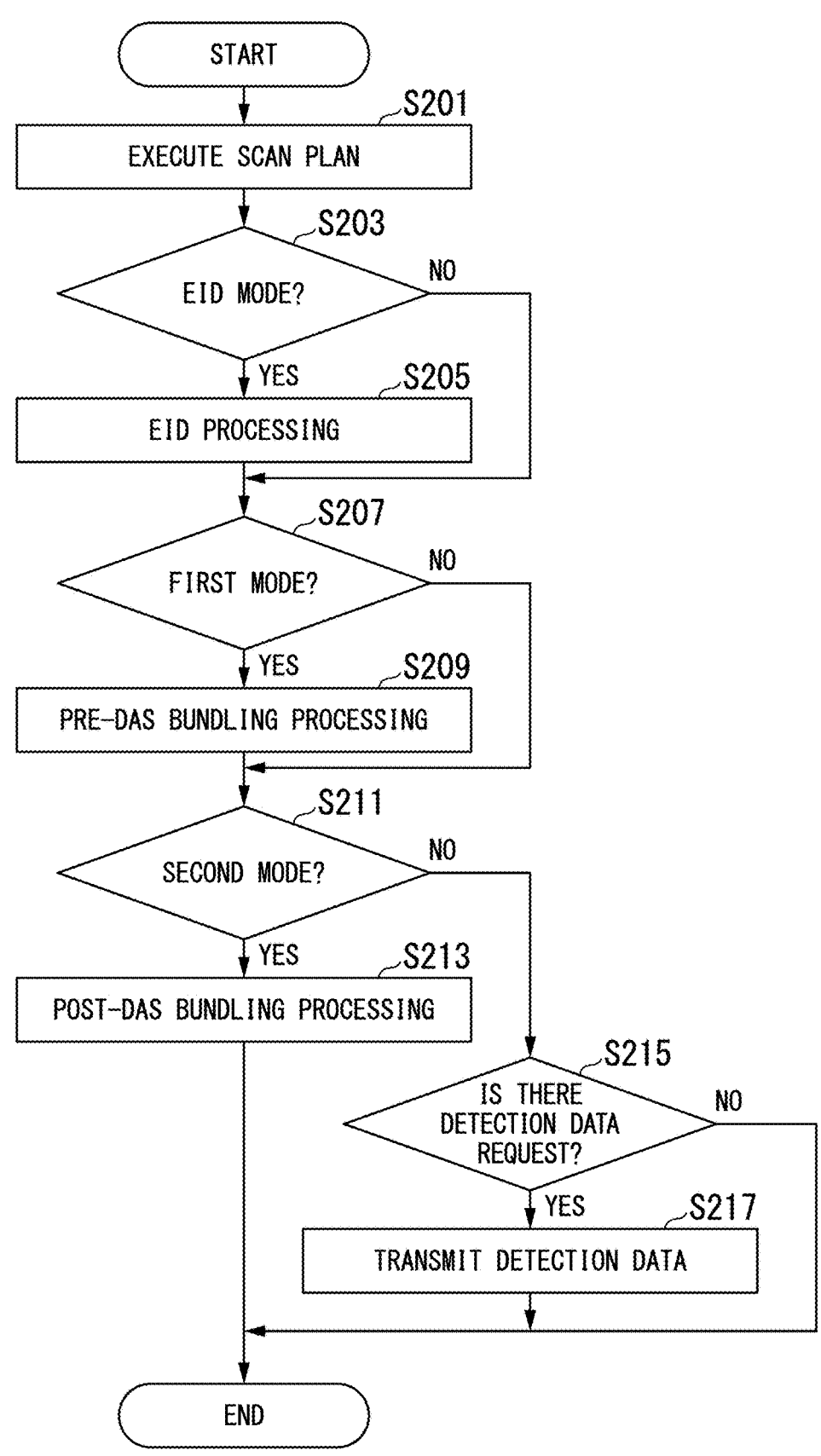
FIG. 8 is a flowchart showing an example of processing in the X-ray CT apparatus 1 according to the second embodiment.

Next, processing in the X-ray CT apparatus 1 according to the second embodiment will be described. FIG. 8 is a flowchart showing an example of processing in the X-ray CT apparatus 1 according to the second embodiment. In the X-ray CT apparatus 1 of the second embodiment, the control device 18 first executes the scan plan 81 stored in the memory 80 (step S201).

Subsequently, the control device 18 determines whether or not the operation mode of the X-ray CT apparatus 1 is the EID mode in the scan plan being executed (step S203). In a case in which it is determined that the operation mode of the X-ray CT apparatus 1 is the EID mode, the switching function 73 switches the collection mode to the EID mode, and the integration circuit 93 performs EID processing (step S205). In EID processing, the integration circuit 93 generates integral data. The output function 77 outputs (transmits) the integral data generated by the integration circuit 93 to the console device 40. In this manner, the output function 77 outputs detection data stored in the memory 80 after outputting detection data aggregated by the aggregation function 76. In a case in which it is determined in step S203 that the operation mode of the X-ray CT apparatus 1 is not the EID mode, the control device 18 causes processing to proceed to step S207.

Subsequently, the control device 18 determines whether or not the current collection mode is the first mode (step S207). In a case in which it is determined that the current collection mode is the first mode, the control device 18 performs pre-DAS bundling processing through the aggregation function 76 in the same manner as in the first embodiment (step S209).

Subsequently, the control device 18 determines whether or not the current collection mode is the second mode (step S211). In a case in which it is determined that the current collection mode is the second mode, the control device 18 performs post-DAS bundling processing through the aggregation function 76 in the same manner as in the first embodiment (step S213).

In a case in which it is determined that the current collection mode is not the second mode and scanning of the subject according to the scan plan has been completed, it is determined whether or not there has been a detection data request according to transmission of detection data request information from the console device 40 (step S215). In a case in which it is determined that there has been detection data request information, the output function 77 outputs (transmits) detection data stored in the memory 80 to the console device 40 and ends the processing shown in FIG. 8. In a case in which it is determined that there is no detection data request information, the control device 18 ends the processing shown in FIG. 8.

The X-ray CT apparatus of the second embodiment has the same effects as the X-ray CT apparatus 1 of the first embodiment. Furthermore, the X-ray CT apparatus of the second embodiment includes the integration circuit 93 (integration type CT circuit) in addition to the collection circuit 92 (photon counting type CT circuit). Therefore, the subject can be scanned in a manner depending on various requests.

For example, in a case in which a subject is scanned in the EID mode, the influence of noise is greater than in a case in which the subject is scanned in first mode or second mode (hereinafter, a PCD mode), and thus the X-ray dose value tends to increase. For example, at the time of examining a subject, a past CT image and a newly captured CT image may be compared, and if scanning is possible in the PCD mode as in the X-ray CT apparatus of the second embodiment, scanning in EID mode may also be required.

In such a case, in the X-ray CT apparatus of the second embodiment, when a subject is scanned at the time of reconstructing a CT image used for comparison with a past CT image, the EID mode in which the X-ray dose value relatively increases is used, but in a case in which other CT images are captured, the PCD mode in which the X-ray dose value is low can be used. Therefore, it is possible to easily reconstruct a CT image for comparison with a past CT image and to reduce the overall radiation exposure of the subject. The collection mode (EID mode) may be designated on the basis of a scan plan and may also be designated by an operation of the operator through the input interface, or the like according to the intention of the operator.

Note that the amount of detection data in the EID mode is approximately equivalent to the amount of data for one energy bin in the PCD mode, and is smaller than the amount of detection data in the second mode, for example. Furthermore, noise in the EID mode tends to be greater than noise in the PCD mode. Therefore, it is desirable that the EID mode be used, for example, at the time of reconstructing a CT image used for comparison with a past CT image and other CT images be reconstructed using the PCD mode.

Furthermore, in the EID mode, the aggregation function 76 generates detection data including CT values, and the reconstruction function 53 in the processing circuitry 50 of the console device 40 reconstructs an image on the basis of the CT values. On the other hand, the aggregation function 76 counts, for example, the number of X-ray photons collected in one energy bin in the first mode. The detection data aggregated by the aggregation function 76 includes the number of X-ray photons collected in the first mode and data of representative values (median, average, and the like) obtained from the range of pulse height values set for the energy bin.

The reconstruction function 53 in the processing circuitry 50 of the console device 40 multiplies the number of X-ray photons included in the detection function by a representative value to calculate a value (hereinafter, a CT equivalent value) that serves as an index at the time of reconstructing an image, and reconstructs an image on the basis of the CT equivalent value. Therefore, the image reconstructed in the EID mode and the image reconstructed in the first mode are similar, but are not always the same. For this reason, when reconstructing a CT image used for comparison with a past CT image, for example, an image reconstructed in the first mode can be used, but an image reconstructed in the EID mode has higher accuracy as a comparison target.

According to at least one embodiment described above, it is possible to reduce the amount of data transmitted by including a collector that collects data corresponding to the energy of a material, an adjuster that adjusts conditions for the data at the time of collecting the data, a bundler that bundles the data distinguished in some of a plurality of energy bins, an aggregator that aggregates the data collected by the collector and the data bundled by the bundler, a switcher that switches aggregation of the aggregator between aggregation of the data collected by the collector and aggregation of the data bundled by the bundler.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus, comprising:
a gantry; and
a control device held by the gantry, the control device comprising processing circuitry configured to:
collect data corresponding to energy of X-ray photons;
adjust conditions for the data at a time of collecting the data;
bundle the data distinguished in some of a plurality of energy bins;
aggregate count data of the X-ray photons of each energy bin according to the collected data and aggregate the count data of the X-ray photons according to the bundled data; and
switch collection modes for collecting data between a first mode and a second mode based on mode setting information included in a scan plan, a number of energy bins set in the first mode being less than a number of energy bins set in the second mode.

2. The X-ray CT apparatus according to claim 1, wherein the processing circuitry is further configured to adjust at least one of the number of energy bins or numerical criteria regarding the energy at a time of distinguishing the data in the energy bins.

3. The X-ray CT apparatus according to claim 2, wherein the processing circuitry is further configured to adjust the number of energy bins to be smaller in the first mode than in the second mode.

4. The X-ray CT apparatus according to claim 3, wherein the processing circuitry is further configured to adjust the number of energy bins to be one in the first mode.

5. The X-ray CT apparatus according to claim 1, wherein the processing circuitry is further configured to:
output the aggregated count data; and
store the collected data in a buffer.

6. The X-ray CT apparatus according to claim 5, wherein the processing circuitry is further configured to store the collected data in the buffer in the first mode.

7. The X-ray CT apparatus according to claim 6, wherein, after outputting the aggregated count data, the processing circuitry is further configured to output the data stored in the buffer.

8. The X-ray CT apparatus according to claim 1, wherein the processing circuitry is further configured to calculate integral data by integrating the collected data corresponding to the energy of the X-ray photons.

9. The X-ray CT apparatus according to claim 1, wherein the processing circuitry is further configured to:
calculate integral data by integrating the collected data corresponding to the energy of the X-ray photons in a third mode; and
switch between the first mode, the second mode, and the third mode.

10. The X-ray CT apparatus according to claim 1, wherein the gantry comprises a rotating frame configured to rotatably hold an X-ray tube and an X-ray detector, and
wherein the control device is held by the rotating frame.

11. The X-ray CT apparatus according to claim 10, wherein the gantry further comprises a fixed frame provided with a receiver, and
wherein the processing circuitry is further configured to output the aggregated count data to the receiver through optical communication.

12. The X-ray CT apparatus according to claim 11, further comprising a console device that includes a memory, and wherein the receiver is configured to transfer the aggregated count data to the console device for storage in the memory.

13. A data processing method using an X-ray CT apparatus comprising a gantry and a control device held by the gantry, the data processing method, using a computer serving as the control device, the method comprising:

collecting data corresponding to energy of X-ray photons;

adjusting conditions for the data at a time of collecting the data;

bundling the data distinguished in some of a plurality of energy bins;

aggregating count data of the X-ray photons of each energy bin according to the collected data and aggregate the count data of the X-ray photons according to the bundled data; and switching collection modes for collecting data between a first mode and a second mode based on mode setting information included in a scan plan, a number of energy bins set in the first mode being less than a number of energy bins set in the second mode.

14. A non-transitory computer-readable storage medium storing a program used in an X-ray CT apparatus comprising a gantry and a control device held by the gantry, the program causing a computer serving as the control device to:

collect data corresponding to energy of X-ray photons;

adjust conditions for the data at a time of collecting the data;

bundle the data distinguished in some of a plurality of energy bins;

aggregate count data of the X-ray photons of each energy bin according to the collected data and aggregate the count data of the X-ray photons according to the bundled data; and switch collection modes for collecting data between a first mode and a second mode based on mode setting information included in a scan plan, a number of energy bins set in the first mode being less than a number of energy bins set in the second mode.

* * * * *